United States Patent [19]

Willms et al.

[11] Patent Number: 5,618,728
[45] Date of Patent: Apr. 8, 1997

[54] PROCESS FOR THE ENZYMATIC CLEAVAGE OF 2-AMINO-4-METHYL-PHOSPHINOBUTYRAMIDE DERIVATIVES

[75] Inventors: Lothar Willms, Hofheim; Klaus Bartsch, Königstein, both of Germany

[73] Assignee: Hoechst Schering AgrEvo GmbH, Berlin, Germany

[21] Appl. No.: 478,561

[22] Filed: Jun. 7, 1995

[30] Foreign Application Priority Data

Jun. 26, 1994 [DE] Germany .................. 44 22 045.6

[51] Int. Cl.$^6$ ................... C12P 41/00; C12P 9/00; C12P 13/04
[52] U.S. Cl. ........................... 435/280; 435/106
[58] Field of Search ................ 435/280, 106

[56] References Cited

U.S. PATENT DOCUMENTS

| | | | |
|---|---|---|---|
| 4,389,488 | 6/1983 | Grabley et al. | 435/280 |
| 5,051,525 | 9/1991 | Willms et al. | 558/145 |
| 5,374,736 | 12/1994 | Zeiss | 548/119 |

FOREIGN PATENT DOCUMENTS

| | | |
|---|---|---|
| 0193113 | 9/1986 | European Pat. Off. |
| 0346658 | 5/1989 | European Pat. Off. |
| 0382114 | 8/1990 | European Pat. Off. |
| 0193113B1 | 1/1992 | European Pat. Off. |
| 0382113B1 | 9/1994 | European Pat. Off. |
| 2717440A1 | 4/1977 | Germany . |
| 2939269A1 | 9/1979 | Germany . |
| 73-85538 | 2/1972 | Japan . |
| 74-31890 | 7/1972 | Japan . |
| WO89/10969 | 11/1989 | WIPO . |

OTHER PUBLICATIONS

Dixon, M. et al., *Enzymes*, Chapter VIII, "Enzyme Inhibitors" Pharma Biochemie u. Mikr., Longmans 2nd Ed. pp. 346–353.

Kruizinga, W.H. et al., "Synthesis of Optically Pure α-Alkylated α-Amino Acids and a Single-Step Method for Enantiomeric Excess Determination" J. Org. Chem. 1988, 53, 1826–1827.

Sasaki, M. et al., "Synthesis of Skeleton of Antitumor Quassinoid" Bull. Chem. Soc. Jpn, 61, 3587–3605, Oct. 1988.

The Chemical Science Society of Japan, Oct., 1988, pp. 3699–3704 by Ivan A. Natchev entitled "Organophosphorus Analogues and Derivatives of the Natural L-Amino Carboxylic Acids and Peptides. I. Enzymatic Synthesis of D-, DL-, and L-Phosphinothricin and Their Cyclic Analogues".

*Primary Examiner*—Michael G. Wityshyn
*Assistant Examiner*—S. Saucier
*Attorney, Agent, or Firm*—Curtis, Morris & Safford, P.C.

[57] ABSTRACT

Process for the enzymatic separation of phosphinothricin derivatives, which comprises treating a mixture of D- and L-phosphinothricin derivatives of the formulae (I) and (II)

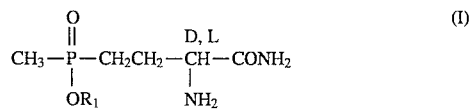

and

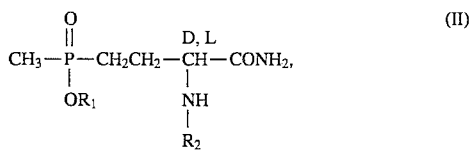

with a hydrolytically active enzyme in an aqueous or aqueous-organic medium.

11 Claims, 2 Drawing Sheets

PROCESS FOR THE ENZYMATIC CLEAVAGE OF 2-AMINO-4-METHYL-PHOSPHINOBUTYRAMIDE DERIVATIVES

L-2-Amino-4-methylphosphinylbutanoic acid—hereinbelow termed L-phosphinothricin or L-PTC—or salts thereof with bases or acids are, as has been disclosed in DE-A 2939269, the active component of the racemate which is chemically readily accessible, i.e. 2-amino-4-methylphosphinylbutanoic acid. Tests described in DE-A 2717440 have shown that L-phosphinothricin has a pronounced herbicidal activity against a broad spectrum of weeds, while the D-form is inactive. This resulted in the need to develop a usable process which allows the L-form to be made accessible by an economic process.

It has already been disclosed that L-PTC can be obtained by acid hydrolysis (JA-OS 73-85538) or by enzymatic degradation (JA-OS 74-31890) of L-PTC-alanyl-alanine, an antibiotic of microbial origin which is known from the literature.

Moreover, there are known processes based on the enzymatic resolution of chemically synthesized, racemic PTC precursors. DE-A 2939269 describes a process in which N-acyl-PTC, in particular N-acetyl-PTC, is cleaved with the aid of acylases which can be obtained from specifically bred microbe strains of the genus Pseudomonas, Streptomyces or Aspergillus.

In the following text, reference is made to a number of microorganisms which have been deposited in public repositories and given identification numbers. These microorganisms and their repository numbers are tabulated below for sake of convenient reference:

| ORGANISM | IDENTIFICATION NO. |
| --- | --- |
| Arthrobacter sp. | ATCC 31652 |
| Acinetobacter calcoatiens | DSM 3875 |
| Mycobacterium nesaurum | ATCC 25725 |
| Enterobacter aerogenes | DSM 9164 |
| Klebsiella oxytoca | DSM 9162 |
| Klebsiella trevisanii | DSM 9163 |
| Corynebacterium aquaticum | DSM 9171 |
| Rhodococcus rubropertinctus | ATCC 21930 |
| Rhodococcus rhodochrous | ATCC 33278 |
| Corynebacterium sp. | ATCC 31662 |

Identification numbers with the prefix "ATCC" refer to deposits at the American Type Culture Collection Patent Depository, 12301 Parklawn Drive, Rockville, Md. 20852, U.S.A., while identification numbers with the prefix "DSM" refer to deposits at the DSM Deutsche Sammlung von Mikroorganism und Zellkulturen GmbH, Mascheroder Weg 1b, D-38124, Braunschweig, Germany.

EP 0 382 113 describes a variety of processes in which racemic 2-acylamino-4-(alkoxy-methylphosphinyl)butanecarboxylic esters are cleaved enzymatically by means of esterases, and 2-acylamino-4-(alkoxy-methylphosphinyl)-butanoic esters and -butanamides by means of acylases.

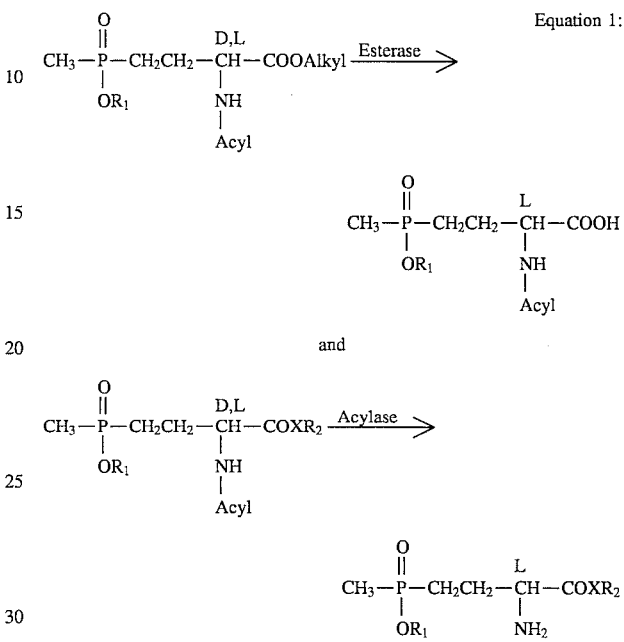

Equation 1

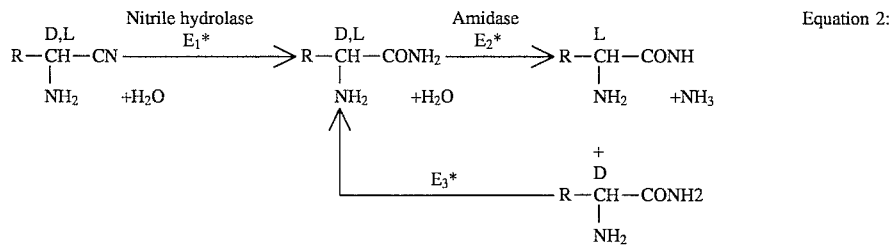

Equation 2

R=for example —$CH_2C_6H_5$;
$E_1^*$=aminonitrile hydrolase
$E_2^*$=L-amino acid amide amidase
$E_3^*$=D-amino acid amide racemase WO 8910969 A describes a process in which in particular aryl-substituted racemic aminonitriles are first converted into the corresponding D,L-amino acid amides by incubation with an Acinetobacter calcoatiens (DSM 3875) culture and these products are cleaved in a further step by an L-amino acid amidase, such as, for example, Arthrobacter ATCC 31652, to give L-amino acid, the remaining D-amino acid amide simultaneously being racemized by an amide racemase (equation 2).

Even though all these synthetic steps may be carried out in succession or simultaneously, the process appears as rather unpromising for realizing using three different enzymes industrial-scale production of L-amino acids due to the complexity of the sub-processes.

A possibility of cleaving amino acids having phosphorus-containing radicals is not suggested. This is probably due to the fact that P(V)-containing compounds, in particular derivatives of the formula R'R"P(O)OR''', simulate the transition state of an enzymatically hydrolyzed carboxylate due to their steric arrangement (see M. Dixon, E. Webb in "Enzymes" e. Edition, Longmans, Green & Co LTD, London 1964, pages 346–352) and, accordingly, may have a deactivating effect.

J. Org. Chem. 53, 1826 (1988) furthermore describes a process for the enzymatic separation of racemic α-alkylated amino acid amides using *Mycobacterium nesaurum* (ATCC 25725) to give α-alkylated L-amino acids and the corresponding D-amino acid amides, but the enantiomeric excesses obtained are only moderate.

EP-A 193 113 describes the hydrolysis of racemic α-amino acid amides, such as, for example, D,L-phenylalanine amide, by microorganisms such as, for example, Pseudomonas, to give L-amino acids. The remaining D-amino acid amide is racemized by strong bases, such as NaOH, and recirculated into the process. Again, the patent description lacks any suggestion regarding the use of phosphorus-containing amino acid derivatives.

Finally, Bull. Chem. Soc. Japan 61, 3599 (1988) describes the hydrolysis of L-2-acetamido-4-(methylphosphinyl)butanamide or of L-2-acetamido-4-(ethoxymethylphosphinyl)butanamide to give L-2-acetamido-4-(methylphosphinyl)butanoic acid and L-2-acetamido-4-(ethoxymethylphosphinyl)butanoic acid by the enzyme glutaminase. However, these amidase reactions are expressly carried out only with the L-configurated phosphinothricin amide derivatives in question and thus provide no route for the economical synthesis of L-phosphinothricin from inexpensive racemic precursors.

Based on the abovementioned prior art, it could not have been predicted that L-phosphinothricin can be efficiently synthesized enzymatically using readily accessible phosphinothricin amides which are modified on the phosphinic acid moiety.

The invention provides a process for the enzymatic conversion of PTC derivatives which comprises treating a mixture of D- and L-PTC derivatives of the formulae (I) and (II)

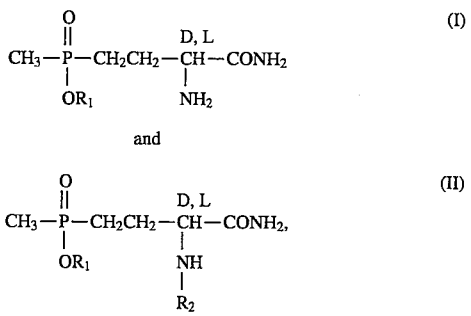

in which $R^1$ is unbranched or branched $(C_1-C_{20})$-alkyl which is unsubstituted or substituted by one or more halogen radicals, such as fluorine, chlorine, bromine or iodine, or mono- or polysubstituted by $(C_1-C_8)$-alkoxy, or is $(C_3-C_8)$-cycloalkyl which can be substituted by one or more groups selected from the group consisting of $(C_1-C_4)$-alkyl, $(C_1-C_4)$-alkoxy and halogen, or is $(C_3-C_{10})$-alkenyl, $(C_3-C_{10})$-alkynyl or benzyl, and $R^2$ is formyl, unbranched or branched $(C_1-C_{20})$-alkylcarbonyl which is unsubstituted or substituted in the alkyl moiety by one or more radicals selected from the group consisting of hydroxyl, halogen, $(C_1-C_4)$-alkoxy, $(C_1-C_4)$-alkylthio and phenyl which can be substituted by up to 3 radicals selected from the group consisting of $(C_1-C_{12})$-alkyl, $(C_1-C_{12})$-alkoxy, halogen, nitro and $CF_3$, or is benzoyl or benzoyl which is substituted by 1 to 3 radicals selected from the group consisting of $(C_1-C_{12})$-alkyl, $(C_1-C_{12})$-alkoxy, halogen, nitro and $CF_3$, with a hydrolytically active enzyme in an aqueous or aqueous-organic medium using a selectively active L-amino acid amide-cleaving enzyme or microorganism.

It is possible to employ racemic amino acid amide derivatives, or amino acid amide derivatives whose L-form has been enriched, of the formulae (I) and (II). The D-phosphinothricin amide derivative which remains can be racemized, for example by the action of bases, and recirculated into the process.

The reaction can also be carried out in the presence of a D-amino acid amide racemase so that pure L-phosphinothricin derivatives are finally obtained.

Of particular interest is a process according to the invention which comprises using a mixture of D- and L-PTC derivatives of the abovementioned formulae (I) and/or (II) in which $R^1$ is unbranched or branched $(C_1-C_{10})$-alkyl or $(C_1-C_{10})$-alkyl which is substituted by halogen, such as fluorine, chlorine or by $(C_1-C_4)$-alkoxy, or is $(C_5-C_6)$-cycloalkyl, and $R^2$ is hydrogen, formyl, unbranched or branched $(C_1-C_{10})$-alkylcarbonyl which is unsubstituted or substituted in the alkyl moiety by one or two radicals selected from the group consisting of hydroxyl, halogen, $(C_1-C_4)$-alkoxy, $(C_1-C_4)$-alkylthio, phenyl or phenyl which is substituted by 1 to 3 radicals selected from the group consisting of $(C_1-C_4)$-alkyl, $(C_1-C_4)$-alkoxy and halogen, or is benzoyl or benzoyl which is substituted by 1 to 3 radicals selected from the group consisting of $C_1-C_4$-alkyl, $C_1-C_4$-alkoxy and halogen.

Preferred is a process according to the invention which comprises the use of a mixture of D- and L-PTC derivatives of the abovementioned formulae (I) and/or (II) in which $R^1$ is unbranched or branched $(C_1-C_{10})$-alkyl and $R^2$ is hydrogen, $(C_1-C_{10})$-alkylcarbonyl which is substituted by phenyl or by phenyl which is mono- to trisubstituted and whose 1 to 3 substituents are selected from the group consisting of $(C_1-C_4)$-alkyl, $(C_1-C_4)$-alkoxy and halogen, preferably phenacetyl, or is benzoyl.

$(C_1-C_6)$-Alkyl is, in particular, methyl, ethyl, 1-propyl or 2-propyl, n-, i-, tert- or 2-butyl, 3-methyl-but-2-yl, n-, i-, tert-, 2- or 3-pentyl, n-hexyl or a hexyl stereoisomer. $C_1-C_6$-Alkoxy is, in-particular, $(C_1-C_6$-alkyl$)$-oxy, the alkyl radical having the abovementioned meaning.

Unless defined in greater detail, halogen is a radical fluorine, chlorine, bromine and iodine, preferably fluorine and chlorine, in particular chlorine.

The cleavage according to the invention can be realized by N-acyl cleavage of the D,L-PTC derivatives of the formulae (I) and (II) in which $R^1$ and $R^2$ are as defined above.

This amidase cleavage of the amino acid amide derivatives of the formula (I) gives the corresponding phosphine ester-protected L-phosphinothricin of the formula (III)

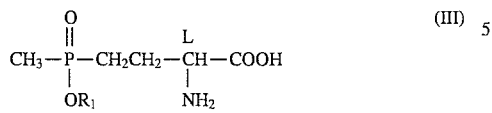

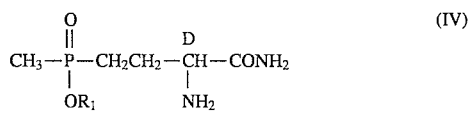

which can be isolated from the unreacted amide of the formula IV in a manner known per se by a known route, for example by extractive removal of the unreacted D-PTC derivative from the acid which has been cleaved off at a pH in the acidic range, in which process the L-PTC derivative remains in the aqueous solution in the form of the ammonium salt and can subsequently be isolated by evaporating the aqueous solution to dryness. Other feasible possibilities are, inter alia, separation by means of crystallization, distillation or chromatography.

The amidase cleavage of these N-acyl-amino acid derivatives of the formula (II) gives the corresponding phosphine ester-protected L-N-acylphosphinothricin of the formula V in the form of a mixture with unreacted D-N-acylamino acid amide of the formula VI.

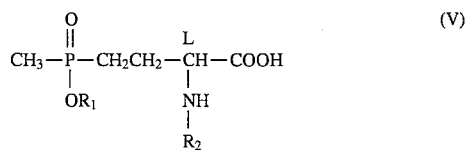

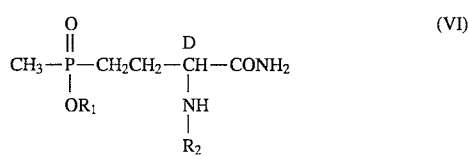

The enzymatically hydrolyzed L-PTC derivative V can be isolated successfully in a customary manner or a manner which is known in principle, such as, for example, by means of crystallization, distillation, column or ion exchange chromatography and, in particular, by rapid extraction of the unreacted D-PTC derivative from the aqueous phase (the pH preferably being between 9 and 11, in particular between 9.5 and 10.5) with the aid of a suitable organic solvent, if appropriate at a reduced temperature of 0° to 10° C., the L-PTC derivative which originates from the amide cleavage remaining in the aqueous phase in the form of the carboxylate salt.

After the D-derivative has been separated off, the L-PTC derivative is subjected to chemical hydrolysis analogously to customary methods, for example using aqueous dilute mineral acid at a temperature of 20° C. up to the boiling point of the solution, the reaction times being 1 to 24 hours. A suitable mineral acid is, for example, a hydrohalic acid or sulfuric acid, in particular dilute to concentrated hydrochloric acid.

However, organic acids are also highly suitable in individual cases. Chemical total hydrolysis gives not only L-PTC, but also the carboxylic acid which corresponds to the acyl radical $R^2$, it being possible to remove this carboxylic acid from the aqueous-acidic solution by distillation or by extraction with a suitable organic solvent.

The D-PTC derivatives which remain can be purified from by-products of the enzymatic hydrolysis by extraction processes, distillation, crystallization or chromatography and subjected again to enzymatic hydrolysis in the form of a D,L-mixture, if appropriate after racemization, for example thermally or by the action of a base, such as an alcoholate in alcoholic solution. As a rule, such a racemization with a base is a particularly mild procedure.

The abovementioned enzymes can be employed in free form or after immobilization by customary processes or processes known to the expert. The substrate in question is employed in the form of a solution or suspension in the aqueous medium. Concentrations of 0.1% up to a saturated solution (where the process is carried out in a suspension) are possible. Equally, the addition of water-soluble solvents, such as methanol, is possible in individual cases, as is a procedure involving a two-phase mixture with the addition of organic solvents which are not soluble in water.

As a rule, the reaction temperature for the enzymatic cleavages is 10°–60° C. preferably 20°–40° C. For example, the process can be carried out batchwise or continuously as a column process.

The enzymatic hydrolysis is preferably carried out at a pH of 5 to 12, in particular pH 6 to 10, it also being possible to carry out the process in individual cases at pH 5 to 7 so as to suppress nonspecific hydrolysis of the carboxylate or carboxamide.

The course of the reactions can be monitored for example by HPLC by monitoring the loss of substrate. In individual cases, in particular when carboxylic esters are cleaved, the course of the reaction can also be monitored by other, simple methods, for example by monitoring the amount of base which has to be metered in until the pH remains constant.

The L-compound content in the enzymatic cleavage product can be determined with the aid of HPLC in a manner known in principle (D. Asward, Analytical Biochemistry 137, 405–409 (1984) after the compound has been subjected to alkaline or acidic hydrolysis to give L-PTC, followed by derivatization.

The starting materials of the formula II are known or can be prepared by processes known per se (cf. EP 0 382 114).

The starting materials of the formula I were previously unknown and therefore also are a subject of the present patent application. The synthesis of these compounds is described in the experimental part by way of example.

The term D or L in the optionally derivatized PTC derivatives merely indicates the configuration on the carbon atom which is in the α-position relative to the carboxyl group and which is linked to the optionally protected amino group. As a rule, these D- or L-PTC derivatives are not pure enantiomers but diastereomer mixtures, due to the additional chiral center on the phosphorus atom in the $R^1$-protected PTC derivatives.

Surprisingly, it has emerged that it is essentially only the configuration on the abovementioned α-carbon atom which is important for the enzymatic cleavage. After hydrolysis of the radical $R^1$, the chiral center on the phosphorus atom is virtually lost due to the rapid proton exchange between OH and O.

The process according to the invention for the resolution of D,L-PTC derivatives and for the preparation of L-PTC is distinguished by low amounts of salt produced on efficient separation of the substrate/product mixture. If the D-PTC derivative which is obtained after the enzymatic separation is not desired, it can be racemized readily and under mild conditions, if appropriate without previous isolation, and thus be used again for enzymatic separation.

The process according to the invention can preferably be carried out using microorganisms which synthesize amidases. Examples of such microorganisms are *Enterobacter aerogenes* (DSM 9164), *Klebsiella oxytoca* (DSM 9162), *Klebsiella trevisanii* (DSM 9163), *Corynebacterium aquaticum* (DSM 9171), *Rhodococcus rubropertinctus* (ATCC 21930), *Rhodococcus rhodochrous* (ATCC 33278), *Arthrobacter sp.* (ATCC 31652) and *Coryne-bacterium sp.* (ATCC 31662).

When employing the PTC derivatives which are provided with a P-O acid function which is ester-protected according to the invention, then a particular and unexpected advantage is the possibility of using even commercially available amidases for the enantioselective cleavage of the PTC derivatives. As a rule, inhibition of the hydrolytic activity by the phosphinic ester or even the side reaction of a hydrolysis of the phosphinic ester is not observed in this process, which is surprising. In this enzymatic amide cleavage, the protection of the phosphinic acid in the form of an ester has a positive effect on the conversion rate or, in individual cases, makes the enzyme accept the substrate in the first place.

A) Starting materials

EXAMPLE A1

Figure 1:
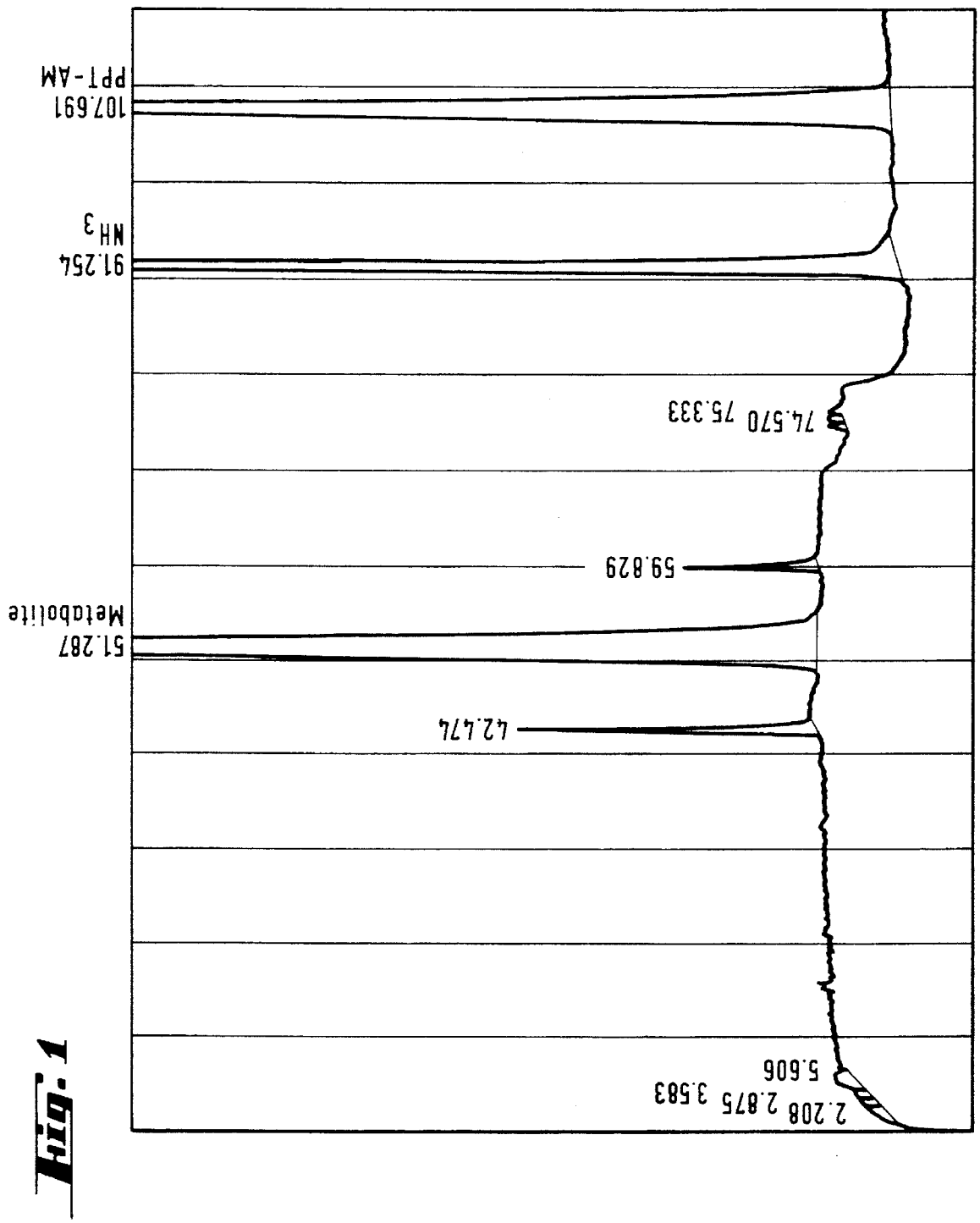
FIG. 1 is an amino acid profile of a culture supernatant from *Enterobacter aerogenes* DSM 9164 grown with PPT-AM as sole nitrogen source.

D,L-2-Amino-4-(1-butoxy-(methyl)phosphinyl)butanamide (formula I: $R_1$=n-$C_4H_9$)

a) D,L-2-Amino-4-(1-butoxy-(methyl)phosphinoyl)butanonitrile (preparation analogous to U.S. Pat. No. 5,051,525 or EP 0 382 114).

52.25 g (0.200 mol) of D,L-2-acetoxy-4-(1-butoxy(methyl)phosphinoyl)butyronitrile are added at 30° C. in the course of 2 hours to 60 ml of ammonia solution (25%).

The reaction mixture is subsequently extracted using dichloromethane, and the extract is dried over sodium sulfate and evaporated in a rotary evaporator. This gives 32.1 g (73.5% of theory) of a yellowish oil which is employed in the next synthetic step without purification.

b) D,L-2-Amino-4-(1-butoxy-(methyl)phosphinoyl)butanamide 16.14 g of D,L-2-amino-4-(1-butoxy-(methyl)phosphinoyl)butanonitrile (0.075 mol) are saturated with 60 g of HCl gas at room temperature in 100 ml of formic acid. After 2 hours, the reaction mixture is concentrated, the residue is taken up in water, and the mixture is brought to a pH of 8 using saturated sodium bicarbonate solution. The solution is subsequently washed twice using dichloromethane, and the aqueous phase is subsequently evaporated in a rotary evaporator and repeatedly boiled down with methanol. After the methanol extracts have been concentrated, the oil which remains is chromatographed on silica gel in methanol/dichloromethane (3:7).

This gives 14.7 g (83.1% of theory) of D,L-2-amino-4-(1-butoxymethyl)phosphinoyl)butanamide in the form of a colorless oil.

$^1$H NMR (CDCl$_3$): 0.94 (t, J=Hz, 3H); 1.48 (d, J=14 Hz, 3H), overlapped by 1.32–1.48 (m, 2H), 1.64 (m, 2H), 1.8–2.1 (n, 4H); 2.5 (s, NH$_2$); 3.52 (t, J=..Hz), 3.96 (m, 2H); 6.38 (s, 1H); 7.42 (g, 1H). $^{12}$p NMR(D$_2$..): 62.4 (s) ppm.

BIOLOGICAL EXAMPLES

Substances

D,L-2-Amino-4-(methyl)(n-butoxy)phosphinoylbutanamide=PPT-AM

D,L-N-Acetyl-4-(methyl)(n-butoxy)phosphinoyl-2-aminobutanamide=PPT-Ac

EXAMPLE 1

Degradation of PPT-AM and PPT-Ac in the Soil 10 g sample of soil from various origins (sandy, embankment gravel, woodland humus, meadow, garden humus, loam) were dried, screened and treated with 1.2 ml of 100 mM solutions of each of the two test substances, pH=7.0. The batches were incubated in the dark at room temperature for 14 days.

To analyze the degradation behavior, 0.5 g samples were taken after 1, 2, 4, 6, 8, 12 and 14 days and extracted for 2×30 minutes at 60° C. using 2×0.5 ml of water. The combined supernatants were examined in an amino acid analyzer with ninhydrin post-column derivatization (Biotronic LC$_{5001}$) (in the case of PPT-AM) or by means of HPLC (column: Aminex HPX-87H/eluent: 0.01 H$_2$SO$_4$, 10% of acetonitrile, or 0.1% of trifluoroacetate, 10% of aceto-nitrile/elution: isocratic detection: 195 nm and 210 nm respectively) (in the case of PPT-Ac).

Control experiments on sterile soil were carried out (incubation at 200° C. for 4 hours). It emerged that both test substances are degraded in the microbially active soils, with a half-life of approximately 1–2 days. In each case one metabolite accumulates in an approximately equimolar ratio to the starting material. However, further degradation of the test compounds was not found within an experimental time of 2 weeks. No reaction of the two amides was detectable in the sterile soils.

EXAMPLE 2

Enrichment Cultures of Soil Microorganisms with PPT-AM or PPT-Ac as the Sole Nitrogen Source 1 g batches of the soils described in Example 1 were extracted with 10 mM NaCl, 10 mM sodium phosphate buffer, pH=7.0, at room temperature and the supernatants used for inoculating the following medium:

0.2% of glucose
5 mM succinate
10 mM glycerol
1 g/l of NH$_4$Cl
2.5 g/l of K$_2$HPO$_4$, pH=7.2
0.06 g/l of MgSO$_4$
0.01 g/l of NaCl
1 ml/l of trace element solution
10 mM PPT-AM or PPT-Ac
Trace element solution:
1 g/l of FeSO$_4$×7 H$_2$O
0.22 g/l of MnSO$_4$×H$_2$O
0.1 g/l of H$_3$BO$_3$
0.1 g/l of Na$_2$MoO$_4$×2 H$_2$O
0.18 g/l of ZnSO$_4$×7
0.16 g/l of CuSO$_4$×5 H$_2$O
0.1 g/l of CoCl$_2$×6 H$_2$O 1 ml/l of 1N HCl.

2 ml batches of these cultures were incubated at 28° C. and 200 rpm for 2–3 days and, after growth had taken place, subjected to further passages while reducing the nitrogen source NH$_4$Cl stepwise (1 g/l→0.5→0.1 g/l→0 g/l). This allowed several enrichment cultures to be obtained which are capable of growing with PPT-AM and PPT-Ac, respectively, as the sole-nitrogen source.

To obtain pure cultures, single colonies were isolated from the enrichment cultures after plating them on the appropriate agar medium, and these single colonies were then multiplied in liquid medium and again streaked on agar plates to assess the purity. The pure cultures obtained were identified as follows:

Utilization of PPT-AM and PPT-Ac as sole nitrogen sources:

Enterobacter aerogenes (DSM Deposit Number: DSM 9164)

Utilization of PPT-Ac as sole nitrogen source:

Klebsiella oxytoca (DSM Deposit Number: DSM 9162)

Klebsiella trevisanii (DSM Deposit Number: DSM 9163)

Corynebacterium aquaticum (DSM Deposit Number: DSM 9171)

EXAMPLE 3

Screening of Other Microorganisms for Utilization of PPT-AM or PPT-Ac as Sole Nitrogen Source Using the procedure described in Example 2, a series of microorganisms from strain collections were screened for utilization of the two amides as sole nitrogen source. The following strains which are capable of utilizing exclusively PPT-AM as substrate were found:

Rhodococcus rubropertinctus, ATCC 21930

Rhodococcus rhodochrous, ATCC 33278

Arthrobacter sp., ATCC 31652

Corynebacterium sp., ATCC 31662

EXAMPLE 4

Characterization of the Degradation Reactions 10 ml cultures of the strains described in Examples 2 and 3 were grown in minimal medium of Example 2 at 28° C. and 200 rpm for 2–3 days with the relevant amide substrate as sole nitrogen source. When the cells had reached the late phase of logarithmic growth, they were centrifuged off and the culture supernatants were analyzed in the amino acid analyzer (in the case of PPT-AM cultures) or by HPLC (in the case of PPT-Ac cultures) as outlined in Example 1.

Figure 2:
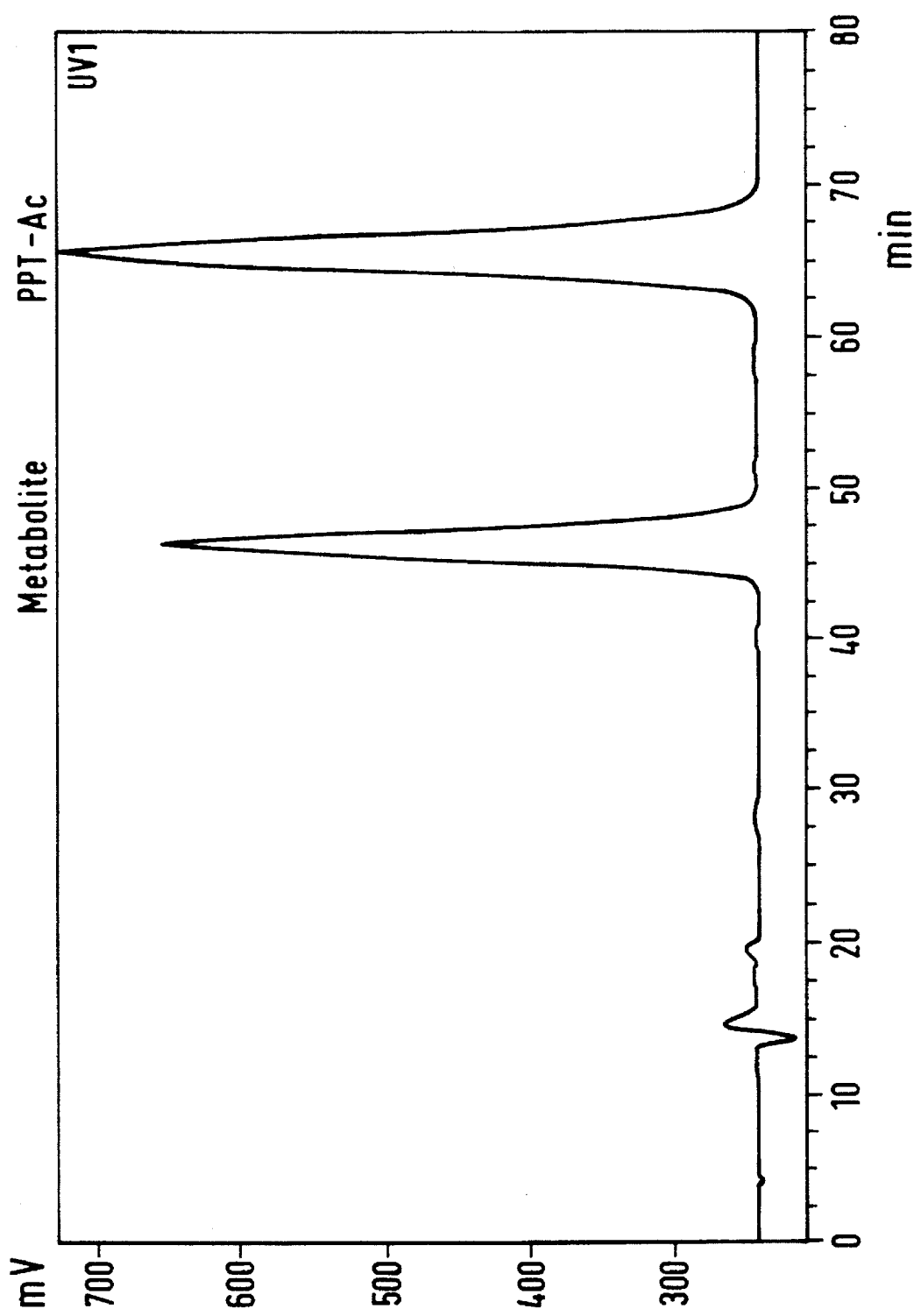
FIG. 2 is an HPLC profile of a culture supernatant from *Enterobacter aerogenes* DSM 9164 grown with PPT-Ac as sole nitrogen source.

With both amide substrates, the formation of a metabolite was observed which is in an approximately equimolar ratio to the unreacted starting compound (see FIGS. 1 and 2).

Despite the excess of carbon sources in the medium, a further reaction of the racemic amides PPT-AM and PPT-Ac was not observed, which suggested that the degradation reactions are stereoselective. Furthermore, an enrichment of ammonia was detected in the culture supernatants (see FIG. 1), ammonia being formed as a product in amidase reactions.

EXAMPLE 5

Identification of the PPT-Ac Metabolite, and Determination of the Enantiomeric Ratios The culture supernatants from Example 4 (PPT-Ac) were concentrated by a factor of 10 by means of lyophilization. Approximately 10 mg each of the metabolites and of the unreacted starting compounds were isolated from these solutions as follows:

PPT-Ac and metabolite M: preparative HPLC, conditions see Example 1, elution: 0.1% of trifluoroacetate, 10% of acetonitrile, detection: 210 nm.

The isolated substances were concentrated by lyophilization and subsequently analyzed by mass spectroscopy. This allowed the molecular structures of the metabolite to be determined. The substance was identified as:

M=N-acetyl-4-(methyl)(n-butoxy)phosphinoyl-2-aminobutanoic acid.

To examine the enantiomeric purity, the metabolite and the unreacted amides were hydrolyzed with HCl to give the free phosphinothricin (PPT). The enantiomeric ratios of the resulting PPT samples were determined after derivatization with the aid of chiral HPLC (D. Aswad, Analytical Biochemistry, 137, 405–409, 1984).

The results are shown here for the strain Enterobacter aerogenes (DSM Deposit Number: DSM 9164):

| metabolite: | 95.7% of L-PPT | unreacted PPT-AM: | 3.3% of L-PPT |
|---|---|---|---|
| | 4.3% of D-PPT | | 96.7% of D-PPT |

Comparable results were also obtained for the other strains described herein.

The tests reveal that the reaction type found is a stereoselective hydrolysis of the racemic amides employed to give the corresponding L-carboxylic acids, catalyzed by L-specific amidases.

EXAMPLE 6

Enantioselective Amide Cleavage of PPT-Ac By Means of Biotransformation

Klebsiella oxytoca (DSM Deposit Number: DSM 9162) was cultured in an Erlenmeyer flask in 100 ml of medium of Example 2 at 28° C. and 200 rpm for 2 days with 10 mM PPT-Ac as sole nitrogen source. The cells were subsequently centrifuged off for 10 minutes at 500 rpm, washed 1×in 50 ml of 10 mM NaCl, 10 mM sodium phosphate buffer, pH=7.0, and resuspended in the same buffer with 30 mg/ml of D,L-PPT-Ac at a concentration of c=50 mg/ml.

The biotransformation batch (total volume 12 ml) was incubated in an Erlenmeyer flask at 28° C. and 200 rpm for 15 hours and the reaction supernatant was subsequently analyzed by HPLC (see Example 1).

The N-acetyl-4-(methyl) (n-butoxy)phosphinoyl-2-aminobutanoic acid content was 14.5 mg/ml. The enantiomeric purity of the product formed corresponded to the figure given in Example 5.

We claim:

1. A process for the enzymatic conversion of DL-phosphinothricin amide to L-phosphinothricin, which comprises treating a mixture of D- and L-phosphinothricine amide of the formulae (I) and/or (II)

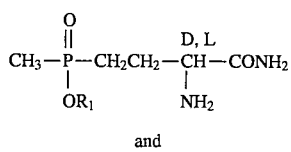

and

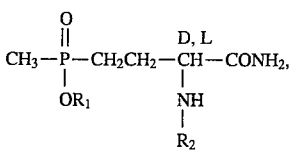

in which

R¹ is unbranched or branched $(C_1-C_{20})$-alkyl which is unsubstituted or substituted by one or more halogen radicals, or mono- or polysubstituted by $(C_1-C_8)$-alkoxy, or is $(C_3-C_8)$-cycloalkyl which can be substituted by one or more groups selected from the group consisting of $(C_1-C_4)$-alkyl, $(C_1-C_4)$-alkoxy and halogen, or is $(C_3-C_{10})$-alkenyl, $(C_3-C_{10})$-alkynyl or benzyl, and R² is formyl, unbranched or branched $(C_1-C_{20})$-alkylcarbonyl which is unsubstituted or substituted in the alkyl moiety by one or more radicals selected from the group consisting of hydroxyl, halogen, $(C_1-C_4)$-alkoxy, $(C_1-C_4)$-alkylthio and phenyl which can be substituted by up to 3 radicals selected from the group consisting of $(C_1-C_{12})$-alkyl, $(C_1-C_{12})$-alkoxy, halogen, nitro and $CF_3$, or is benzoyl or benzoyl which is substituted by 1 to 3 radicals selected from the group consisting of $(C_1-C_{12})$-alkyl, $(C_1-C_{12})$-alkoxy, halogen, nitro and $CF_3$, in an aqueous or aqueous-organic medium with at least one microorganism which is selected from the group consisting of *Enterobacter aerogenes* (DSM 9164), *Klebsiella oxytoca* (DSM 9162), *Klebsiella trevisanii* (DSM 9163), *Corynebacterium aquaticum* (DSM 9171), *Rhodococcus rubropertinctus* (ATCC 21930), *Rhodococcus rhodochrous* (ATCC 33278), Arthrobacter sp. (ATCC 31652), and Corynebacterium sp. (ATCC 31662) which has an L-amino acid amidase which selectively cleaves the L-phosphinothricin amide of formula (I) and/or (II).

2. The process as claimed in claim 1, wherein the compounds according to formula (I) and/or (II) are treated with at least one L-amino acid amidase from said microorganisms.

3. The process as claimed in claim 1, wherein racemic phosphinothricin amide or phosphinothricin amide whose L-form has been enriched, of the formulae (I) and/or (II) are employed.

4. The process as claimed in claim 1, wherein the compounds according to formulae (I) and/or (II) are enzymatically treated with a D-amino acid amide racemase.

5. The process as claimed in claim 1, wherein

R¹ is unbranched or branched $(C_1-C_{10})$-alkyl or $(C_1-C_{10})$-alkyl which is substituted by halogen, such as fluorine, chlorine or by $(C_1-C_4)$-alkoxy, or is $(C_5-C_6)$-cycloalkyl, and R² is hydrogen, formyl, unbranched or branched $(C_1-C_{10})$-alkylcarbonyl which is unsubstituted or substituted in the alkyl moiety by one or two radicals selected from the group consisting of hydroxyl, halogen, $(C_1-C_4)$-alkoxy, $(C_1-C_4)$-alkylthio, phenyl or phenyl which is substituted by 1 to 3 radicals selected from the group consisting of $(C_1-C_4)$-alkyl, $(C_1-C_4)$-alkoxy and halogen, or is benzoyl or benzoyl which is substituted by 1 to 3 radicals selected from the group consisting of $C_1-C_4$-alkyl, $C_1-C_4$-alkoxy and halogen.

6. The process as claimed in claim 1, wherein

R¹ is unbranched or branched $(C_1-C_{10})$-alkyl and

R² is hydrogen, $(C_1-C_{10})$-alkylcarbonyl which is substituted by phenyl or by phenyl which is mono- or trisubstituted and whose 1 to 3 substituents are selected from the group consisting of $(C_1-C_4)$-alkyl, $(C_1-C_4)$-alkoxy and halogen, or is benzoyl.

7. The process as claimed in claim 1, wherein

R¹ is unbranched or branched $(C_1-C_{10})$-alkyl and

R² is phenacetyl.

8. The process as claimed in claim 1, wherein

R¹ is unbranched or branched $(C_1-C_6)$-alkyl, selected from the group consisting of methyl, ethyl, 1-propyl, 2-propyl, n-butyl, i-butyl, tert-butyl, 2-butyl, 3-methylbut-2-yl, n-pentyl, i-pentyl, tert-pentyl, 2-pentyl, 3-pentyl, and any stereoisomeric hexyl.

9. The process as claimed in claim 1, wherein halogen in R¹ and/or R² is fluorine, chlorine, bromine, or iodine.

10. The process as claimed in claim 1, wherein halogen in R¹ and/or R² is fluorine or chlorine.

11. The process as claimed in claim 1, wherein halogen in R¹ and/or R² is chlorine.

* * * * *